United States Patent [19]

Ware

[11] 4,253,835
[45] Mar. 3, 1981

[54] POST AND SLEEVE ARRANGEMENT

[75] Inventor: Ormond H. Ware, St. Petersburg, Fla.

[73] Assignee: Mike Z. Nemethy, Treasure Island, Fla. ; a part interest

[21] Appl. No.: 80,574

[22] Filed: Oct. 1, 1979

[51] Int. Cl.³ .............................................. A61C 5/08
[52] U.S. Cl. ...................................... 433/220; 264/16
[58] Field of Search .............. 433/220, 221, 219, 225, 433/173, 74, 40; 264/16, 17, 19

[56] References Cited

U.S. PATENT DOCUMENTS

| | | | |
|---|---|---|---|
| 6,114 | 2/1849 | Clark | 433/221 |
| 277,934 | 5/1883 | Richmond | 433/221 |
| 764,528 | 7/1904 | Haldeman | 433/220 |
| 900,363 | 10/1908 | Fredericks | 433/220 |
| 965,246 | 7/1910 | Stallman | 433/221 |
| 1,062,048 | 5/1913 | Spain | 433/220 |
| 1,583,459 | 5/1926 | Hansen | 433/220 |
| 3,629,943 | 12/1971 | Gindea | 433/220 |
| 3,797,113 | 3/1974 | Brainin | 433/173 |

FOREIGN PATENT DOCUMENTS

| | | | |
|---|---|---|---|
| 386152 | 6/1908 | France | 433/221 |
| 475999 | 6/1915 | France | 433/221 |
| 745982 | 5/1933 | France | 433/221 |
| 58913 | 12/1939 | Norway | 433/221 |

*Primary Examiner*—Gene Mancene
*Assistant Examiner*—John J. Wilson
*Attorney, Agent, or Firm*—William A. Newton

[57] ABSTRACT

Disclosed is a dental arrangement and method for restoring broken teeth which require a crown and a retention post for securing the crown in a post hole formed in the tooth. The post hole is dimensioned to receive a first sleeve, which in turn is dimensioned to receive the retention post. By using the sleeve for confirming a desirable post hole size, and for centering the retention post during the making of the impression, a sufficient margin of error is built into the space between the post hole and the retention post to allow the placement of cement. A wax sealed second sleeve, with a short post therein, is used in making a die of the tooth.

15 Claims, 6 Drawing Figures

POST AND SLEEVE ARRANGEMENT

FIELD OF INVENTION

The present invention is directed toward securing crowns to broken down teeth using a retention post.

DESCRIPTION OF THE PRIOR ART

Various procedures exist in the prior art for restoring broken teeth which require a crown and a retention post for securing the crown, by use of cement, in a post hole formed in the broken down tooth. One method involves the simultaneous casting of the retention post and a core formed thereon in one unit. The disadvantage of this procedure is that due to inaccurate tolerances, the retention post may hang up on the walls of the post hole and not seat properly. An additional disadvantage of this procedure requires the dental patient to make an additional office visit, once to cement the post-core and then a second time to take an impression of the core for forming the crown.

A second prior art procedure provides for the casting of a core to a steel retention post. This procedure eliminates the seating problems of the first described procedure, because the steel post is prefabricated and does not change dimensions when the core is cast to it and mechanically bonded thereto. However, this second procedure has the disadvantage of requiring an extra office visit to cement the post-core and then to take an impression of the core and tooth for the crown.

A third prior art procedure involves the casting of the crown-post, without the casting of a core. This eliminates the previously described extra office visit found in the first two described procedures. However, alignment of neighboring teeth often prevent the crown from fitting.

A fourth prior art procedure involves casting the post and core, then casting the crown as a separate unit. This method eliminates the above described extra office visit. However, since the post and core is cemented first, there is a layer of cement below the core and then below the crown. The two cement layers, plus inherent casting inaccuracies, may prevent the crown from fitting.

Patents representing the prior art are U.S. Pat. Nos. 3,797,113; 3,629,943; 0,900,363; 0,965,246 and French Patent Nos. 475,999; 386,152; and 745,982.

SUMMARY OF THE INVENTION

The present invention is directed toward a dental arrangement and method for use in restoring endodonitically treated, broken down teeth, which require a crown and a retention post protruding therefrom for securing the crown in a post hole formed in the broken down tooth. The dental arrangement includes a first sleeve having an outer diameter smaller than the diameter of the post hole and having an inner diameter larger than the outer diameter of the retention post. The first sleeve and the retention post are inserted in the post hole, with the retention post extending above the top of the first sleeve. The first sleeve substantially centers the retention post within the post hole, while an impression is made of the top of the tooth and the protruding retention post. Upon removal of the impression from the top of the tooth, the retention post remains embedded in the impression material. Subsequently, a second, longer sleeve is placed over the embedded retention post. A short post is placed in the second sleeve and the second sleeve is then sealed with a wax. A die stone is now poured over the sealed second sleeve so as to form a die in the shape of the tooth above the gum line, with the second sleeve and the retention post therein. The laboratory technician "waxes up" a crown or a core over the retention post. The crown or core can be readily removed from the die for subsequent casting, due to the retention post being easily removed from the second sleeve. Moreover, the use of the second sleeve allows removal of the retention post without breaking off bits of die stone that will prevent the retention post from seating completely back into the post hole. The primary advantage of the use of the first sleeve becomes apparent when the retention post is cemented in the post hole. Due to the respective sizing of the post hole, the sleeve and the retention post and due to the centering of the retention post by the first sleeve during the impression, a space is provided between the retention post and the walls of the tooth in the post hole. Hence, this space provides room for the placement of cement around the retention post, even though the retention post might expand during casting. Moreover, this space provides for a margin of error in the alignment of the tooth, and therefore, the center post, with the post hole.

BRIEF DESCRIPTION OF THE DRAWINGS

Further objects and advantages of the present invention will become apparent as the following description proceeds, taken in conjunction with the accompanying drawings in which.

DESCRIPTION OF THE PREFERRED EMBODIMENT

Figure 1:
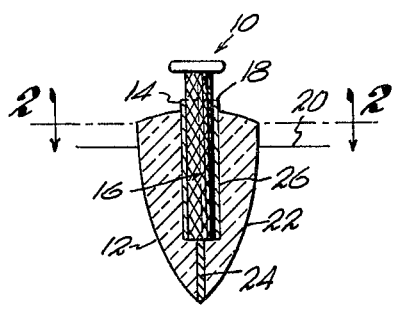
FIG. 1 is a cross-sectional view of a tooth having the dental device of the present invention shown therein.

Referring to FIG. 1, there is disclosed a dental arrangement, generally indicated by numeral 10, and method for restoring an endodontically treated tooth 12 that is broken down enough to require a crown and a reinforcement and retention post. The dental arrangement 10 includes a cylinder or first sleeve 14, preferably being 10 to 13 millimeters in length with walls about 0.001 to 0.1 millimeters thick. The first sleeve 14 is preferably formed of metal, but may be of celluloid, plastic, or like material. It should be appreciated that the inside diameter of the first sleeve 14 may vary, and in practice, it is contemplated that the dental manufacturer will provide the first sleeve 14 in a variety of sizes so as to allow the dentist to select a desired size. A knurled retention post 16 formed preferably of plastic or steel, is configured and dimensioned to fit precisely into the first sleeve 14 and to extend approximately 2 to 4 millimeters beyond to top 18 of the first sleeve 14.

Referring to FIG. 1, the endodontically treated tooth 12 is illustrated wherein the crown portion of the tooth is missing, either through tooth decay or through being broken. Typically, the tooth damage occurs above the gum line, illustrated by numeral 20, which leaves the tooth root 22 having a root canal filling 24 therein.

Figure 2:
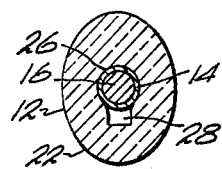
FIG. 2 is a cross-sectional view of the dental device taken along section line 2—2 of FIG. 1.

Referring to FIG. 1, the initial steps of the present invention comprise drilling a post hole 26 at least ten millimeters or two-thirds of the distance down into the tooth root 22, using conventional techniques and equipment. The post hole 26 is cooperatively dimensioned to be approximately 0.001 to 0.1 millimeters larger than the outside diameter of the first sleeve 14. Next, as is illustrated in more detail in FIG. 2, a key-slot 28 is made at the top of the post hole 26 in the tooth 12. The key-slot 28 provides lateral retention to keep the retention post 16, when positioned in the post hole 26, from twisting therein. As shown in FIGS. 1 and 2, after the post hole 26 and key-slot 28 are provided with the desired dimensions, the sleeve 14 with the post 16 disposed therein, are inserted into the post hole 26. It should be appreciated that the insertion of the first sleeve 14 into the post hole 26 allows the dentist to determine whether the post hole 26 is sufficiently sized. If not, further drilling of the post hole 26 will be required. As will be discussed hereinafter, the first sleeve 14 also substantially centers the retention post 16 in the post hole 26.

Figure 3:
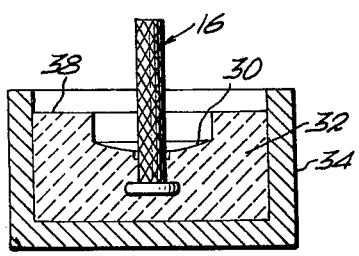
FIG. 3 is a cross-sectional view of the dental device after an impression has been made and removed from the top of the tooth.

Referring to FIG. 3, the next step in the procedure is to make an impression 30 of the tooth 12 disposed above the gum line 20. This is accomplished using conventional impression material 32 which is normally confined within a conventional container 34. The container 34 has an open face so as to leave an exposed surface 38 of the impression material which is deformed during the making of the impression 30 of the tooth 12. As the container 34 is removed from the top of the tooth 12, the retention post 16 is sufficiently embedded in the impression material 32, that it pulls out of the first sleeve 14 and remains embedded in the impression material 32. As illustrated in FIG. 3, the retention post 16 is shown protruding upward in a detached, inverted container 34. The first sleeve 14 is then removed from the post hole 26. It should be appreciated that the first sleeve 14 centrally positioned the retention post while the impression 30 was being made. Hence, the imprint of the retention post 16 is properly positioned.

Figure 4:
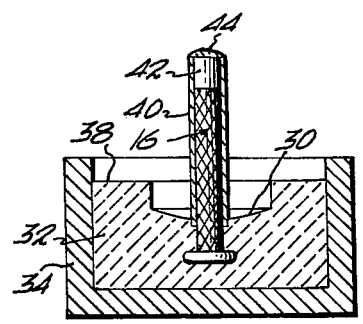
FIG. 4 is a cross-sectional view of the dental device after a second sleeve has been positioned over the embedded retention post.

As illustrated in FIG. 4, a second sleeve 40, which is approximately 2 to 3 millimeters longer than the first sleeve 14, is placed over the embedded retention post 16. A second short post 42 which is approximately 2 to 3 millimeters long, is placed into the end of the second sleeve 40 and sealed off with a preferably "sticky" wax 44. The second sleeve 40 is preferably made out of metal.

Figure 5:
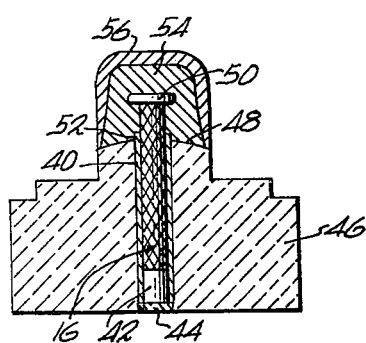
FIG. 5 is a plan view of the dental device surrounded by a die.

As shown in FIG. 5, the impression, as depicted in FIG. 4, is now "poured up" in a well known manner. More specifically, a die stone 46, similar to plaster of Paris, is poured into the impression 30 and over the sealed, second sleeve 40. The die stone 46 is allowed to harden and is removed from the impression 30. It can now be appreciated that the wax 44 prevents the liquid die stone 46 from entering the second sleeve 40. However, the wax 44 creates the added problem of entering the small space between the post 16 and the second sleeve 40. To avoid this complication, the short post 42 is used. Since the range of penetration of the wax in the space between the sleeve 40 and the retention post 16 is limited, such penetration does not generally extend as far as the retention post 16. Hence, the elimination of any contact between the wax 44 and the retention post 16 makes it easy to remove the retention post 16 from the second sleeve 40. More importantly, the adhesion created between the second sleeve 40 and the short post 42 by the wax 44 allows for the short post 42 to form a firm stop for the retention post 16. If the short post 42 had not been used, upon insertion of the retention post 16, the retention post 16 would have proceeded upward to some undetermined point, such point being subject to further settling. The use of a second, longer sleeve 40 not only allows for the inclusion of the short post 42, but it avoids the need of having to trim the sleeve 40 to a very precise longitudinal length that would be mandated by the use of only one sleeve, such as the first sleeve 14. The second sleeve 40 also provides a firm centering support. An added advantage of having the second sleeve 40 in the die stone 46, is that it allows for the retention post 16 to be removed without breaking the die stone 46 and without scouring the walls of the hole formed in the die stone 46. Bits of stone falling into the bottom of the hole in the die stone would prevent the retention post 16 from reseating completely back in the hole.

Referring to FIG. 5, the die stone 46 is shown after it has been removed from the impression 30. By virtue of this procedure, the die stone 46 has a surface defining a die 48 with the shape of the tooth 12 above the gum line 20 with the second sleeve 40 embedded therein. The retention post 16 typically remains implanted in the impression 30, although it should be appreciated that it is completely acceptable if the retention post 16 pulls out of the impression 30. If the retention post 16 remains implanted in the impression 30, the retention post 16 is now removed and placed down into the second sleeve 40 inside the die stone 46, as shown in FIG. 5. When the retention post 16 is placed in the second sleeve 40, its outer flanged extremity 50 is spaced apart from an end 52 of the second sleeve 40.

In the next step of the process, the laboratory technician will "wax up" a crown over the die 48 and the retention post 16. This can be accomplished in several ways. As shown in FIG. 5, the laboratory technician can "wax up" a core 54 over the retention post 16 and the die 48. If the retention post 16 is formed of plastic or a like material, then the retention post 16 and the core 54 can be cast using conventional procedures. If the retention post 16 is formed by a metal or like material, such as steel, then the core will be cast to the steel retention post 16. Alternatively, in certain special situations specified by the dentist, the laboratory technician can "wax up" a crown over the plastic or metal retention post 16, and cast the retention post 16 and/or the crown in one unit, without the intermediate step of forming the core 54. Such special situations might, for example, be when a crown is being placed on a front tooth where the core 54 or crown 56 has a center axis that is substantially aligned with the center axis of the root canal 24. If the intermediate step of casting the core is used, after casting the core 54, the casted core 54 is returned to the second sleeve 40, a crown 56 is then "waxed up" over the casted core 54. Subsequently the crown 56 is cast. The above mentioned procedure of "waxing up" the core 54 or crown 56 is well known in the art, and involves applying a liquid wax that solidifies. After solidification, the wax can then be trimmed and shaped as desired. Likewise, the above-mentioned procedures for casting the retention post 16, core 54 and/or crown 56 are well known in the art. Generally, the item to be cast is surrounded with a conventional investment material, which then hardens. The wax core 54, wax crown 56, and plastic retention post 16 are, in a conventional manner, burned out in an oven. Hence, the investment material has hollow areas which previously held the wax or plastic. Subsequently, a metal alloy, such as gold or a non-precious metal, is centrifugally fed, in a manner well known in the art, into the hollow areas to produce the desired metal crown and post. Porcelain is then applied to the metal crown 56 to give the appearance and the form of real teeth.

Figure 6:
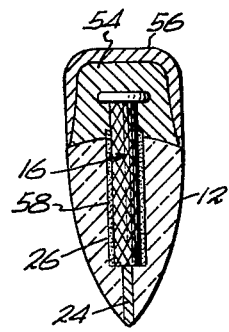
FIG. 6 is a cross-sectional view of the dental device with a crown formed thereon.

Referring to FIG. 6, once the crown 56 has been cast, the retention post 16 is ready for permanent attachment to the tooth 12. It is at this point that one of the main advantages of the use of the first sleeve 14 and the above discussed technique becomes apparent. As previously described, the post hole 26 was dimensioned and configured to receive the first sleeve 14. Since the retention post 16 has a smaller diameter than the outer diameter of the first sleeve 14, a space is provided between the retention post 16 and the walls of the post hole 26. By virtue of this special relationship, cement 58 can be placed in this space. More importantly, the space provides a margin for error in casting and placement in the tooth 12 and provides sufficient room for the cement 58 around the retention post 16. For instance, as is well known in the art, metal can expand, and the cast post 16 may have a greater diameter than the original pre-cast plastic retention post 16. Hence, the spacing originally filled by the first sleeve 14, is now used for any expansion of the cast retention post. This particular advantage is applicable only where the retention post 16 is originally plastic, and then cast. In general, whether the retention post 16 is cast with the crown 56 or core 54, the use of the first sleeve 14 gives the dentist a perfect fit every time since the retention post 16 is assured to go into place completely in the post hole 26.

Although the preferred embodiment shows the retention post 16 and the first sleeve 14 being adapted for sliding engagement with each other, other arrangements are considered within the scope of the present invention. For example, the first sleeve 14 can be made by wrapping the retention post 16 with cellophane or like cellulose material. Prior to making the impression 30, the cellophane is removed from the portion of the retention post extending above the tooth 12. Likewise, prior to pouring the die stone 46 to make the die 48, the cellophane is removed from the portion of the retention post 16 which protrudes from the impression material 32. Also, the first sleeve 14 can be made by encasing the retention post 16 in a chemically dissolvable material, so that portions of it can be removed from the retention post 16 as desired by the application of a dissolving solvent.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A method for making an impression of a broken tooth, the impression to be used to create a die to form a crown for the broken tooth, said method comprising the steps of:

drilling a post hole into the broken tooth for a retention post;

positioning a first sleeve around the retention post;

slidingly inserting the retention post and the first sleeve into the post hole so that the retention post extends beyond the top of the broken tooth;

making an impression of the top of the broken tooth with the retention post and the sleeve inserted in the post hole;

removing the impression from the top of the broken tooth so that the retention post protrudes from the impression;

removing the first sleeve from the post hole;

whereby the use of the first sleeve centers the retention post during the making of the impression and, after the removal of the first sleeve, provides a predetermined spacial area between the retention post and the post hole for the placement of a cement.

2. The method of claim 1, further comprising, pouring a die stone over the impression and the retention post to form a die;

waxing up a crown on the die and retention post;

casting the crown;

cementing the retention post, with the crown mounted thereon, in the post hole.

3. The method of claim 1, wherein said step of slidingly inserting the retention post further includes positioning the retention post to extend above the first sleeve.

4. The method of claim 3, providing a second sleeve which has a longer longitudinal dimension than the first sleeve;

after making the impression, placing the second sleeve over the retention post which is protruding from the impression;

next, positioning a relatively short post in the end of the second sleeve;

next, positioning a wax seal over the end of the second sleeve.

5. The method of claim 4, after placement of the wax seal, pouring a die stone over the impression and the sealed second sleeve to provide a die having the shape of the tooth above the gum line and having the sealed second sleeve and the retention post disposed therein.

6. The method of claim 5, after forming a die, waxing up a core on the retention post for subsequent casting.

7. The method of claim 6, providing the retention post formed of a plastic material, casting the core and the retention post as one unit.

8. The method of claim 5, after forming the die, waxing up a crown on the retention post for subsequent casting.

9. The method of claim 8, providing the retention post formed of a plastic material;

casting the retention post and a crown as one unit.

10. The method of claim 1, wherein said step of slidingly inserting the retention post and the first sleeve includes slidingly inserting the retention post into the first sleeve.

11. A method for making a die from an impression of a broken tooth, the die being used to form a crown for the broken tooth, said method comprising the steps of:

making an impression of the top of the broken tooth and inserting an end of a retention post therein;

after making the impression, placing a sleeve over the retention post, which is protruding from the impression, so that the sleeve extends beyond the end of the retention post;

next, positioning a relatively short post in the end of the sleeve, next, pouring a liquid material over the impression and the sleeve to form a die wherein the retention post can be slidingly removed from the sleeve.

12. In the method of claim 11, placing a seal over the end of the sleeve before pouring the liquid material to make the die.

13. In the method of claim 12, removing the die and the sleeve embedded in the die from the impression;

removing the impression from the retention post.

14. In the method of claim 13, after the steps of removing the impression from the die and the retention post, waxing up a core on the retention post and the die for subsequent casting.

15. In the method of claim 13, after the steps of removing the impression from the die and the retention post, waxing up a crown on the retention post and the die for subsequent casting.

* * * * *